United States Patent [19]

Strande et al.

[11] Patent Number: 5,962,626
[45] Date of Patent: Oct. 5, 1999

[54] SURFACTANTS

[75] Inventors: Per Strande; Harald Dugstad; Balin Balinov, all of Oslo; Jan Alfheim, Hagan; Joseph Arukwe, Oslo, all of Norway

[73] Assignee: Nycomed Imaging AS, Norway

[21] Appl. No.: 08/977,630

[22] Filed: Nov. 25, 1997

[30] Foreign Application Priority Data

Nov. 25, 1996 [GB] United Kingdom ............... 9624548

[51] Int. Cl.$^6$ ............... C08G 63/48; C11D 9/00
[52] U.S. Cl. ............... 528/295.5; 528/272; 528/301; 252/108; 252/DIG. 1; 252/DIG. 7
[58] Field of Search ............... 528/272, 295.5, 528/301; 252/108, DIG. 1, DIG. 7

[56] References Cited

U.S. PATENT DOCUMENTS 5,658,374  8/1997  Clover ............... 106/2

*Primary Examiner*—Samuel A. Acquah
*Attorney, Agent, or Firm*—Bacon & Thomas PLLC

[57] ABSTRACT

The present invention provides a polyethylene glycol (PEG) ester surfactant comprising at least one polyethylene glycol moiety and at least one fatty acyl moiety characterized in that said moieties are linked by a linkage incorporating a biodegradable methylene diester unit of formula (I)

$$-CO.O.C(R^1)(R^2).O.CO- \qquad (I)$$

where $R^1$ and $R^2$ may, for example, each be a hydrogen atom or a monovalent organic group attached through a carbon atom or $R^1$ and $R^2$ together may, for example, form a divalent organic group attached through carbon atoms.

10 Claims, No Drawings

SURFACTANTS

The present invention is concerned with non-ionic surfactants, more particularly with polyoxyethylene fatty acid ester surfactants which exhibit controllable levels of biodegradability.

The use of polyoxyethylene/polyethylene glycol (PEG) moieties as hydrophilic components of non-ionic surfactants is extremely well known, examples including PEG ethers of the type R.(O.CH$_2$.CH$_2$)$_n$.OH where R represents a long chain aliphatic group or mixture of such groups and n is an integer, e.g. as marketed under the trademark Brij; PEG esters of the type R.CO.(O.CH$_2$.CH$_2$)$_n$.OH where R and n are as defined above, e.g. as marketed under the trademark Myrj; and polyoxyethylene-polyoxypropylene block copolymers, e.g. as marketed under the trademark Pluronic. PEG fatty acid esters have attracted particular interest by virtue of the ease with which a wide range of surfactant properties may be achieved by appropriately, balancing the length of the hydrophobic fatty acyl moiety and the degree of polymerisation of the hydrophilic PEG segment, and have been employed in many cosmetic, pharmaceutical and other industrial applications, for example as antistats, emulsifiers, defoamers, wetting agents, solubilisers, conditioning agents, lubricants and detergents.

In view of their widespread use it is clearly desirable that such PEG fatty acid ester surfactants should exhibit a significant degree of biodegradability in order to minimise the risk of environmental accumulation. Whilst the ester linkage between the PEG and fatty acid moieties will ultimately be hydrolytically cleavable, surfactants exhibiting a higher rate of biodegradation may possess a number of significant advantages, as discussed in greater detail hereinafter.

WO-A-9204392, the contents of which are incorporated herein by reference, discloses that methylene diester units having the formula (I)

—CO.O.C(R$^1$)(R$^2$).O.CO—    (I)

(where R$^1$ and R$^2$ each represents a hydrogen atom or a monovalent organic group attached through a carbon atom or R$^1$ and R$^2$ together form a divalent organic group attached through carbon atoms) are particularly rapidly degraded by common esterase enzymes, both in the natural environment (e.g. as a result of bacterial attack) and in the human or non-human animal body, but are stable in the absence of such enzymes. The specification describes a wide range of biodegradable polymers containing such units, in which the ester groups may be carboxylate or carbonate esters, i.e. such that the diester units have the formula (II)

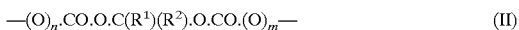
—(O)$_n$.CO.O.C(R$^1$)(R$^2$).O.CO.(O)$_m$—    (II)

(where R$^1$ and R$^2$ are as defined above and m and n, which may be the same or different, are each 0 or 1).

Polymers comprising a water-soluble non-polypeptide polymer backbone rendered at least substantially water-insoluble by the presence of lipophilic side chains attached to the polymer backbone through linkages comprising units of formula (I) are described in WO-A-9318070. Such polymers are rendered water-soluble and thereby dispersible or excretable as appropriate upon biodegradative cleavage of the methylene diester units and thus of the lipophilic side chains.

WO-A-9506518 discloses block and graft copolymer surfactants containing biodegradable linkages of formula (II) as defined above, typically as part of the repeating unit of one of the polymer blocks.

Biodegradable polymers consisting of repeating units of formula (III)

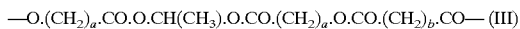
—O.(CH$_2$)$_a$.CO.O.CH(CH$_3$).O.CO.(CH$_2$)$_a$.O.CO.(CH$_2$)$_b$.CO—    (III)

(where a represents an integer in the range 9–19 and b represents an integer in the range 1–8) are described in WO-A-9607434.

The present invention is based on the findings that PEG ester surfactants in which the linkage between the PEG and fatty acyl moieties incorporates a methylene diester unit may exhibit a range of advantageous properties. In particular, such surfactants are readily biodegradable to yield non-toxic products, typically fatty acids, simple aliphatic aldehydes and PEGs. This ready biodegradability permits rapid modification of the surface active characteristics of such surfactants by exposing them to esterases, the resulting enzymatic hydrolysis leading to their degradation and consequent diminution or loss of their surface activity. This property of readily modifiable surface activity may be exploited in applications as diverse as release at a targeted site of active ingredients from previously stable emulsions and recovery of metal catalysts from spent reaction mixtures.

Thus according to one aspect of the present invention there are provided PEG ester surfactants comprising PEG and fatty acyl moieties characterised in that said moieties are linked by a linkage incorporating a biodegradable methylene diester unit of formula (I) as hereinbefore defined.

R$^1$ and R$^2$ may, for example, each be hydrogen or a carbon-attached hydrocarbyl of heterocyclic group, for example having 1–20 carbon atoms, e.g. an aliphatic group such as an alkyl or alkenyl group (preferably having up to 10 carbon atoms), a cycloalkyl group (preferably having up to 10 carbon atoms), an araliphatic groups such as an aralkyl group (preferably having up to 20 carbon atoms), an aryl group (preferably having up to 20 carbon atoms) or a heterocyclic group having up to 20 carbon atoms and one or more heteroatoms selected from O, S and N. Such a hydrocarbyl or heterocyclic grouping may carry one or more functional groups such as halogen atoms or groups of the formulae NR$^a$R$^b$, —CONR$^a$R$^b$, —OR$^c$, —SR$^c$ and —COOR$^d$, where R$^a$ and R$^b$, which may be the same or different, are hydrogen atoms, acyl groups or hydrocarbyl groups as defined for R$^1$ and R$^2$; R$^c$ is a hydrogen atom or an acyl group or a group as defined for R$^1$ or R$^2$ and R$^d$ is a hydrogen atom or a group as defined for R$^1$ or R$^2$. Where R$^1$ and R$^2$ represent a divalent grouping this may be an alkylidene, alkenylidene, alkylene or alkenylene group (preferably having up to 10 carbon atoms), which may carry one or more functional groups as defined above.

Preferred methylene diester units include those of formula (I) in which R$^1$ and R$^2$ are selected from hydrogen atoms and lower (e.g. C$_{1-6}$) alkyl groups, e.g. methyl, ethyl or propyl groups. Advantageously both R$^1$ and R$^2$ represent hydrogen atoms or R$^1$ represents hydrogen and R$^2$ represents a methyl group.

The PEG moiety may for example have a molecular weight in the range 200–10,000, corresponding to an average number n of repeating units of about 4–225. Representative PEGS thus include those with average molecular weights of 550, 1000 and 5000, corresponding to n values of ca. 13, 22 and 114 respectively. The PEG moiety may be acylated at one or both ends; the use of mono-acylated PEGs which are alkoxy endcapped, e.g. with a lower alkoxy group such as methoxy, may be preferred.

Fatty acyl moieties may for example contain up to 50 carbon atoms, e.g. 10–30 carbon atoms, for example as in saturated groups such as lauroyl, myristoyl, palmitoyl, stearoyl, eicosanoyl, docosanoyl, tetracosanoyl or melissoyl, and unsaturated groups such as oleoyl or linoleoyl. If desired, the fatty acyl moiety may comprise an aliphatic group carrying two or more acyl groups, for example as in α,ω-alkanedioyl groups such as docosanedioyl, each of which is linked to a PEG moiety.

The acyl group or groups of the fatty acyl moiety conveniently form one of the carbonyl groups of the methylene diester unit of formula (I), the other carbonyl group forming a carbonate ester group with the PEG moiety. Examples of such surfactants according to the invention thus include compounds of formula (IV)

$$R.CO.O.C(R^1)(R^2).O.CO(O.CH_2.CH_2)_n.OR^3 \quad (IV)$$

(where R, $R^1$, $R^2$ and n are as hereinbefore defined, R for example being an alkanoyl group such as palmitoyl or stearoyl, and $R^3$ is a hydrogen atom, an etherifying group, e.g. a lower alkyl group such as a methyl group, or an esterifying group, e.g. an alkanoyl group or a R.CO.O.C.($R^1$) ($R^2$).CO— group) and of formula (V)

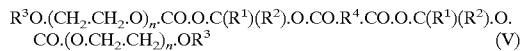
$$R^3O.(CH_2.CH_2.O)_n.CO.O.C(R^1)(R^2).O.CO.R^4.CO.O.C(R^1)(R^2).O.CO.(O.CH_2.CH_2)_n.OR^3 \quad (V)$$

(where $R^1$, $R^2$, $R^3$ and n are as hereinbefore defined and $R^4$ is a divalent aliphatic group, e.g. a $C_{10-30}$ polymethylene group such as 1,20-eicosanediyl).

Such surfactants exhibit comparable surface active properties to known PEG fatty ether and ester surfactants such as those of the Brij and Myrj types and to alkoxy-endcapped simple PEG esters, e.g. α-acyloxy-ω-methoxy PEGS, in certain cases exhibiting surprisingly low critical micellar concentrations relative to known commercially available PEG ether and ester surfactants, but exhibit a substantially higher rate of biodegradation in the presence of esterase enzymes. As noted above, this both enhances their environmental value and renders them particularly useful in applications where it is desirable to modify surface activity during use; it will be appreciated that it may be advantageous in such applications to use surfactants according to the invention as components of surfactant mixtures to obtain a desired level of change in surface active properties. Although biodegradable in the presence of esterases, the surfactants of the invention exhibit stability over a wide range of pH values in the absence of esterases.

In general surfactants according to the invention may, for example, find use in pharmaceuticals, cosmetics, agrochemicals, pesticides and cleaning compositions (e.g. for brewery or dairy equipment), and as powder dispersants, emulsifiers/stabilisers of aqueous dispersions of oils and gases, dispersants for oil spills, components of invert-emulsion or emulsion drilling muds used in stabilising the walls of oil or gas wells, antifoams and controllers of foam formation (e.g. in the paper, pulp and food processing industries).

Surfactants according to the invention may be prepared by any convenient method. Thus, for example, compounds of formula (IV) above may be prepared by (i) reacting a PEG derivative of formula (VI)

$$H.(O.CH_2.CH_2)_n.OR^3 \quad (VI)$$

(where $R^3$ and n are as hereinbefore defined, $R^3$ preferably being an etherifying group such as a methyl group) with a haloalkyl haloformate of formula (VII)

$$X.C(R^1)(R^2).O.CO.X \quad (VII)$$

(wherein $R^1$ and $R^2$ are as hereinbefore defined and the symbols X represent halogen atoms such as chlorine atoms), for example chloromethyl chloroformate or 1-chloroethyl chloroformate, advantageously in the presence of a weak base, for example a tertiary aromatic amine such as pyridine, to yield a compound of formula (VIII)

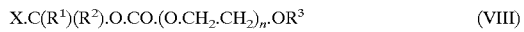
$$X.C(R^1)(R^2).O.CO.(O.CH_2.CH_2)_n.OR^3 \quad (VIII)$$

(where $R^1$, $R^2$, $R^3$, X and n are as hereinbefore defined), and (ii) reacting this product with a fatty acid R.COOH (where R is as hereinbefore defined), advantageously in the presence of a base, for example an alkali metal carbonate such as cesium carbonate. Step (i) may conveniently be conducted in a cyclic ether solvent such as tetrahydrofuran; step (ii) may for example be conducted in an amide solvent such as dimethylformamide.

Compounds of formula (V) may similarly be prepared using an appropriate diacid HOOC.$R^4$.COOH (where $R^4$ is as hereinbefore defined) in step (ii).

It will be appreciated that an inverse order of reaction, e.g. in which an appropriate fatty acid or diacid is reacted with a compound of formula (VII) and the thus-obtained product is reacted with a PEG derivative of formula (VI), may also be used in the preparation of compounds of formulae (IV) and (V).

The following non-limitative Examples serve to illustrate the invention.

EXAMPLE 1 a) O-(Methoxy PEG 550)-O-chloromethyl carbonate

Chloromethyl chloroformate (44 mmol) was added to a stirred solution of dried monomethoxy polyethylene glycol 550 (MPEG) (22 mmol) in anhydrous tetrahydrofuran (150 ml) and pyridine (44 mmol) at ambient temperature. After 3 hours precipitated pyridinium hydrochloride was removed by filtration and the solvent was removed by evaporation. The viscous oily residue was dissolved in ether (150 ml) and the product was precipitated by addition of pentane (200 ml). Decantation of the solvents and drying of the residue under vacuum gave the title compound, a viscous oil, in 70% yield. $^1$H NMR (300 MHz, CDCl$_3$): δ3.37–4.38 (m, MPEG), 5.73 (s, 2H); $^{13}$C NMR (300 MHz, CDCl$_3$): δ59.01, 68.073, 68.615, 70.573, 71.937, 72.244, 76.695, 153.381.

Similar products were also prepared starting from MPEG 1000 and MPEG 5000.

b) (Methoxy PEG 550)oxycarbonyloxymethyl hexadecanoate

A mixture of palmitic acid (1.55 mmol) and cesium carbonate (2 mmol) in dimethylformamide (10 ml) was stirred at ambient temperature for 45 minutes whereafter a solution of O-(methoxy PEG 550)-O-chloromethyl carbonate from (a) above (1.55 mmol) in dimethylformamide (3 ml) was added. The reaction was monitored by HPLC and after 24 hours (95% conversion) the mixture was filtered and the solvent was removed under reduced pressure. The residue was dissolve in chloroform (30 ml) and extracted with saturated aqueous sodium bicarbonate solution (1×15 ml) and water (1×15 ml). Drying (MgSO$_4$), filtration and evaporation of the chloroform phase gave the title compound, a wax, in 90% yield. $^1$H NMR (300 MHz, CDCl$_3$) δ0.85–1.63 (m, 29H), 1.60–1.63 (m, 2H), 3.37–4.34 (m, MPEG), 5.75 (s, 2H); $^{13}$C NMR (300 MHz, CDCl$_3$): δ14.116, 22.681, 24.506, 31.918, 33.897, 59.018, 61.599, 67.644, 68.684, 81.837, 154.000, 172.162.

Similar products were also prepared incorporating MPEG 1000 and MPEG 5000.

EXAMPLE 2 a) O-(Methoxy PEG 550)-O-(1-chloroethyl) carbonate

1-Chloroethyl chloroformate (36.40 mmol) was added to a stirred solution of dried monomethoxy polyethylene glycol 550 (MPEG) (18.00 mmol) in anhydrous tetrahydrofuran (150 ml) and pyridine (36.40 mmol) at ambient temperature. After 3 hours precipitated pyridinium hydrochloride was removed by filtration and the solvent was removed by evaporation. The viscous oily residue was dissolved in ether (150 ml) and the product was precipitated by addition of pentane (200 ml). Decantation of the solvents and drying of the residue under vacuum gave the title compound, a viscous oil, in 70% yield. $^1$H NMR (300 MHz, CDCl$_3$): δ1.93 (d, 3H), 3.40–4.38 (m, MPEG), 6.40 (q, 1H); $^{13}$C NMR (300 MHz, CDCl$_3$): δ25.198, 59.011, 67.810, 68.640, 71:.567, 70.684, 71.932, 84.607, 152.877.

Similar products were also prepared starting from MPEG 1000 and MPEG 5000.

b) 1-[(Methoxy PEG 550) oxycarbonyloxy]ethyl hexadecanoate

A mixture of palmitic acid (1.95 mmol) and cesium carbonate (3 mmol) in dimethylformamide (10 ml) was stirred at ambient temperature for 45 minutes, whereafter a solution of O-(methoxy PEG 550)-O-(1-chloroethyl) carbonate from (a) above (1.95 mmol) in dimethylformamide (3 ml) was added. The reaction was monitored by HPLC and after 24 hours (65% conversion) the mixture was filtered and the solvent was removed under reduced pressure. The residue was dissolved in chloroform (30 ml) and extracted with saturated aqueous sodium bicarbonate solution (1×15 ml) and water (1×15 ml). Drying (MgSO$_4$), filtration and evaporation of the chloroform phase gave the title compound, a wax, in 60% yield. $^1$H NMR (300 MHz, CDCl$_3$): δ0.75–2.52 (m; 29H), 1.29 (d, 3H), 2.10 (m, 2H), 3.07–4.34, (m, MPEG), 6.60 (q, 1H); $^{13}$C NMR (300 MHz, CDCl$_3$): δ14.011, 20.681, 22.508, 24.535, 32.897, 34.000, 59.114, 61.599, 67.644, 68.684, 81.837, 153.000, 169.138.

Similar Products were also prepared incorporating MPEG 1000 and MPEG 5000.

EXAMPLE 3

Bis [(methoxy PEG 1000) oxycarbonyloxmethyl] docosanedioate

Reaction of bis (chlorocarbonyloxymethyl) docosanedioate with two equivalents of monomethoxy polyethylene glycol 1000 in methylene chloride in the presence of pyridine gave the title compound, a wax, in 60% yield. $^1$H NMR (300 MHz, CDCl$_3$): δ1.26 (s), 1.64 (m), 1.741 (s, 36H), 2.34–2.39 (t, 4H), 3.39 (s, 3H), 3.54–3.76 (m, MPEG) 4.32–4.35 (m, 4H), 5.76 (s, 4H), $^{13}$C NMR (300 MHz, CDCl$_3$) δ24.522, 29.034, 29.244, 29.458, 25.624, 29.725, 33.913, 59.038, 67.652, 68.696, 70.593, 70.703, 71.961, 81.853, 154.012, 172.178.

EXAMPLE 4

Measurement of Hydrolysis Rates in the Presence of Pig Liver Esterase

Water (25 ml) and pig liver esterase (Sigma –100 μl) were added, to a 50 ml flask and the pH was adjusted to 8.2 (the optimum pH for pig liver esterase) by addition of 5 mM aqueous sodium hydroxide. Each surfactant to be tested was dissolved in dimethylformamide (200 μl) added to water (1000 μl), and the resulting mixture was added to the flask at ambient temperature with careful stirring. The pH of the flask contents was monitored by means of a pH-stat and maintained constant by continuing addition of 5 mM aqueous sodium hydroxide. Hydrolysis was assumed to be complete when addition of sodium hydroxide was no longer necessary, and the rate of hydrolysis was calculated accordingly. The results are summarised in the following table.

| Product of Example No. [molecular weight of PEG moiety] | Rate of hydrolysis (mmol/min) at pH 8.2 in presence of pig liver esterase | Rate of hydrolysis (mmol/min) at pH 8.2 in absence of pig liver esterase |
|---|---|---|
| 1(b) [550] | 0.87 | 0.04 |
| 1(b) [1000] | 1.30 | 0.04 |
| 1(b) [5000] | 0.69 | 0.04 |
| 2(b) [1000] | 0.79 | |
| 3 [1000] | 0.47 | |
| (Methoxy PEG)hexadecanoate [550] [comparison] | 0.30 | 0.06 |

We claim:

1. A polyethylene glycol ester surfactant comprising at least one polyethylene glycol moiety and at least one fatty acyl moiety characterised in that said moieties are linked by a linkage incorporating a biodegradable methylene diester unit of formula (I)

$$—CO.O.C(R^1)(R^2).O.CO— \quad (I)$$

where $R^1$ and $R^2$ each represents a hydrogen atom or a monovalent organic group attached through a carbon atom or $R^1$ and $R^2$ together form a divalent organic group attached through carbon atoms.

2. A polyethylene glycol ester surfactant as claimed in claim 1 wherein $R^1$ and $R^2$ are selected from the group consisting of hydrogen atoms and $C_{1-6}$ alkyl groups.

3. A polyethylene glycol ester surfactant as claimed in claim 2 wherein $R^1$ represents a hydrogen atom and $R^2$ represents a hydrogen atom or a methyl group.

4. A polyethylene glycol ester surfactant as claimed in claim 1 wherein the polyethylene glycol moiety or moieties have a molecular weight of about 550, 1000 or 5000.

5. A polyethylene glycol ester surfactant as claimed in claim 1 comprising a mono-acylated and alkoxy endcapped polyethylene glycol moiety.

6. A polyethylene glycol ester surfactant as claimed in claim 1 wherein the fatty acyl moiety contains 10 to 30 carbon atoms.

7. A polyethylene glycol ester surfactant as claimed in claim 1 comprising a fatty acyl moiety which is an α,ω-alkanedioyl group.

8. A polyethylene glycol ester surfactant as claimed in claim 1 which is a compound of formula (IV)

$$R.CO.O.C(R^1)(R^2).O.CO(O.CH_2.CH_2)_n.OR^3 \quad (IV)$$

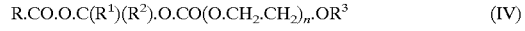

where R is a long chain aliphatic group, $R^1$ and $R^2$ are as defined in claim 1, $R^3$ is a hydrogen atom or an etherifying or esterifying group and n is an integer.

9. A polyethylene glycol ester surfactant as claimed in claim 1 which is a compound of formula (V)

$$R^3O.(CH_2.CH_2.O)_n.CO.O.C(R^1)(R^2).O.CO.R^4.CO.O.C(R^1)(R^2).O.CO.(O.CH_2.CH_2)_n.OR^3 \quad (V)$$

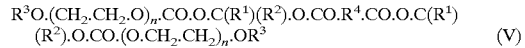

where $R^1$ and $R^2$ are as defined in claim 1, $R^3$ is a hydrogen atom or an etherifying or esterifying group and $R^4$ is a divalent aliphatic group.

10. A polyethylene glycol surfactant as claimed in claim 1 selected from the group consisting of:

(methoxy PEG 550)oxycarbonyloxymethyl hexadecanoate;

(methoxy PEG 1000)oxycarbonyloxymethyl hexadecanoate;

(methoxy PEG 5000)oxycarbonyloxymethyl hexadecanoate;

1-[(methoxy PEG 550)oxycarbonyloxy]ethyl hexadecanoate; and bis[(methoxy PEG 1000) oxycarbonyloxymethyl] docosanedioate.

* * * * *